United States Patent [19]

Jung et al.

[11] Patent Number: 4,755,468

[45] Date of Patent: Jul. 5, 1988

[54] INOCULA OF LOW WATER ACTIVITY WITH IMPROVED RESISTANCE TO TEMPERATURE AND REHYDRATION, AND PREPARATION THEREOF

[75] Inventors: Gerard Jung, Montlhery; Jacques Mugnier, Paris, both of France

[73] Assignee: Rhone-Poulenc S.A., Paris, France

[21] Appl. No.: 777,863

[22] Filed: Sep. 19, 1985

Related U.S. Application Data

[63] Continuation of Ser. No. 452,633, Dec. 23, 1982.

[30] Foreign Application Priority Data

Dec. 29, 1981 [FR] France ............... 81 24403

[51] Int. Cl.$^4$ ............ C12N 11/10; C12N 1/20; A01C 11/06; C05F 11/08
[52] U.S. Cl. ............... 435/178; 435/260; 435/253; 435/878; 47/57.6; 71/7
[58] Field of Search .......... 435/243, 253, 260, 878, 435/177, 178, 179, 180, 182; 47/57.6; 71/6, 7

[56] References Cited

U.S. PATENT DOCUMENTS

| | | | |
|---|---|---|---|
| 1,909,622 | 5/1933 | Matchette | 435/253 |
| 2,901,864 | 9/1959 | Hiler | 47/58 |
| 2,988,455 | 6/1961 | Rosenberg et al. | 106/169 |
| 2,995,867 | 8/1961 | Burton | 71/7 |
| 3,034,968 | 5/1962 | Johnston | 435/253 |
| 3,168,796 | 2/1965 | Scott et al. | 47/1 |
| 3,472,644 | 10/1969 | Woodside et al. | 71/1 |
| 3,616,236 | 10/1971 | Delin | 435/172.1 |
| 3,822,187 | 7/1974 | du Chaffaut et al. | 435/248 |
| 3,898,132 | 8/1975 | Hettrick | 435/253 |
| 4,038,140 | 7/1977 | Jaworek et al. | 435/178 |
| 4,089,746 | 5/1978 | Masri et al. | 435/178 |
| 4,094,097 | 6/1978 | Alexander et al. | 435/240 |
| 4,146,706 | 3/1979 | Hisatsuka et al. | 536/123 |
| 4,155,737 | 5/1979 | Dommergues et al. | 71/7 |
| 4,202,905 | 5/1980 | Asai et al. | 426/1 |
| 4,211,774 | 7/1980 | Kang et al. | 514/61 |
| 4,352,883 | 10/1982 | Lim | 435/178 |
| 4,376,113 | 3/1983 | Suglia et al. | 424/494 |
| 4,434,231 | 2/1984 | Jung | 435/253 |

FOREIGN PATENT DOCUMENTS

| | | | |
|---|---|---|---|
| 521850 | 11/1953 | Belgium | 435/177 |
| 977178 | 11/1975 | Canada | 435/177 |
| 0017565 | 10/1980 | European Pat. Off. | 435/253 |
| 1103676 | 11/1955 | France | 435/177 |
| 1490046 | 7/1967 | France | 435/177 |
| 2453215 | 10/1980 | France | 435/253 |
| 2469861 | 5/1981 | France | 435/177 |
| 48-8830 | 3/1973 | Japan | 435/253 |
| 1177077 | 1/1970 | United Kingdom | 71/7 |
| 1526317 | 9/1978 | United Kingdom | 435/253 |
| 1556584 | 11/1979 | United Kingdom | 435/177 |
| 628143 | 9/1978 | U.S.S.R. | 71/7 |

OTHER PUBLICATIONS

Jung et al.; "Polymer-Entrapped *Rhizobium* as an Inoculant for Legumes"; *Plant Soil*, vol. 65, No. 2, (1982), pp. 219-231.

Bergman et al.; "Simultaneous Granulation and Drying of Biomass and Proteins"; *Chem. Abstr.*, vol. 93, (1980), abstr. 184618g.

M. E. Fraser, "A Method of Culturing *Rhizobium meliloti* on Porous Granules to Form a Pre-Inoculant for Lucerne Seed," 39, *J. Appl. Bact.* 345–51, (1975).

Gault, 21(1), *Newsletter*, 34, (Apr. 1981).

G. A. Hunt et al., "Preservation of Cultures by Drying on Porcelain Beads," 76, *J. Bacteriology*, 453–54, (1958).

H. Leung, "Structure and Properties of Water," 26, (List continued on next page.)

*Primary Examiner*—Elizabeth C. Weimar
*Attorney, Agent, or Firm*—Herbert F. Schwartz; Richard M. Barnes; Teresa L. Solomon

[57] ABSTRACT

Inocula having a long storage life and improved resistance to temperature and rehydration and a method of preparing them are disclosed. The method of the invention comprises admixing a culture medium containing microorganisms of the genus Rhizobium and at least one carbohydrate source in a polymer gel and then lowering the water activity of the resulting inoculum and maintaining the water activity at less than 0.1.

21 Claims, 5 Drawing Sheets

OTHER PUBLICATIONS

*Cereal Foods World*, 350-52, (1981).

Masters, *Spray Drying*, (2d Ed., 1976).

F. Munevar et al., "Growth of *Rhizobium japonicum* Stains at Temperatures Above 27° C.," 42, *Applied and Environmental Microbiology*, 272-76, (1981).

Nilsson, (1957), cited in *Methods for Evaluating Biological Nitrogen Fixation*, (F. Bergersen, ed.), 493.

V. Patrikeyev et al., "Method of Producing Dry Microorganisms," 4, *Microbiology Abstracts: A Industrial Microbiology*, A4153, (1969).

J. Pena-Cabriales et al., "Survival of *Rhizobium* in Soils Undergoing Drying," 43, *Soil Sci. Soc. Am. J.* 962-66, (1979).

M. Salema et al., "Death of Rhizobia on Inoculated Seed," 14, *Soil Biol. Biochem.*, 13-14, (1982).

I. Takata et al., "Screening of Matrix Suitable for Immobilization of Microbial Cells," 2(3), *J. Solid-Phase Biochem.*, 225-36, (1977).

Vincent, "*Rhizobium*", 25, *Newsletter*, 136, (1981).

DAYS STORED AT 55°C

FIG. 3

DAYS STORED AT 55°

INOCULA OF LOW WATER ACTIVITY WITH IMPROVED RESISTANCE TO TEMPERATURE AND REHYDRATION, AND PREPARATION THEREOF

This is a continuation, of application Ser. No. 452,633, filed Dec. 23, 1982, entitled INOCULUMS OF LOW WATER ACTIVITY WITH IMPROVED RESISTANCE TO TEMPERATURE AND REHYDRATION, AND PREPARATION THEREOF.

BACKGROUND OF THE INVENTION

The present invention relates to inocula. More particularly, the present invention relates to inocula containing microorganisms of the genus Rhizobium and which have a low water activity, a long storage life and improved resistance to temperature and rehydration. The invention also relates to a method of preparing such inocula.

Numerous attempts have been made to preserve Rhizobium by dehydration employing various adjuvants, such as on dehydrated balls of porcelain (HUNT, 1958, J. Bacteriol. 76, 453–454); in suspension in dehydrated liquid oils (U.S. Pat. No. 3,034,968); as a dehydrated suspension in oils mixed with talc or kaolin (U.S. Pat. No. 3,168,796); by adsorption on dry granules of plaster (French Pat. No. 1,490,046); as a dehydrated powder on granules of gypsum (FRASER, 1975, J. Appl. Bacteriol. 39, 345); and by using sodium sulfate without water to dehydrate the Rhizobium by formation of a water of crystallization. (NILSSON, 1957, (NILSSON, 1957, cited in *Method for Evaluating Biological Nitrogen Fixation,* F. Bergersen, ed., 493). However, the dehydration processes disclosed in these patents and publications are slow and thus harmful to the survival of the microorganism (e.g., Gault in Newsletter, Vol. 21 (1) April 1981, page 34, and Vincent in Rhizobium, Newsletter, 25, 1981). The steps leading to the dehydrated state can cause the destruction of the Rhizobium.

Methods such as freeze-drying (U.S. Pat. No. 3,168,796) or spray drying (OCHIN, 1980, Dissertation Lille) which use different protective or support substances, such as lactose, milk, cystein hydrochloride, maltodextrin, or finely divided, chemically inert substances of the kaolin type, and activated charcoal, have also been employed. But even with the addition of these protective substances, the drying process, the preservation, and the rehydration are very difficult.

The rehydration of the dehydrated microorganism is particularly difficult. It is known that the progressive absorption of water by a totally dehydrated microorganism is lethal (Amarger, Arch. Mikrobiol 81, 361–366 (1972)). When, for instance, a freeze-dried ampule containing microorganisms is opened, all the microorganisms are dead in less than one week in ambient air. It is, therefore, possible to preserve a portion of the microorganisms by extensive dehydration, but when it is necessary to employ the dehydrated microorganisms in the open field, the use of a solution to rehydrate the microorganisms can create numerous problems.

Attempts have been made to obtain a microorganism enclosed in a polymer which can be preserved indefinitely without special conditions and which is in solid form at the time of its use. This problem has been difficult to solve, and it is believed by those skilled in the art that in order to assure the survival of the microorganisms, a certain amount of humidity must be maintained in the inocula. The culture medium can be added to a support, such as peat, or directly to a polymer gel.

U.S. Pat. No. 4,155,737 discloses the inclusion of a microorganism in a polymer gel which is a polyacrylamide gel or a silica gel. An attempt is made to reduce the water loss, or at least to maintain a water availability (or a water activity) in the inoculum. In addition to the microorganism, the inoculum contains soluble mineral elements, a carbohydrate source such as mannitol, and a nitrogen source such as yeast extract.

In practice, the polymer must be biodegradable or at least non-polluting. For this reason, European Application No. 17,565 discloses the use, as a support, of a matrix having a base of at least one polymer from the group of polysaccharides. This process is characterized by the fact that the gel which contains the microorganism is subjected to a drying, which leaves at least one part of bulk water held in the gel. This drying can be improved by the addition of a substance which has a strong absorption for water, such as a synthetic or natural silica.

In order to assure that a good percentage of the microorganisms survive, the water activity should generally be maintained at a value which is preferably above 0.85. However, at the optimum moisture content required in the inocula referred to in these patents, for instance for the survival of Rhizobium, the germination of fungi spores and the development of molds and contaminants is a problem with nonsterile products. For most molds, the water activity range within which development is possible is generally between 0.80 and 0.95, but certain molds which are referred to as xerophytic or "osmotolerant" are capable of developing at lower water activities ($a_w = 0.6$–$0.7$).

In order to assure the microbiological stability of inocula having an optimal water content, it has been necessary to prepare and store the inocula in sterile form or to subject the inocula to cold storage. The stability of the refrigerated inocula results both from the lowering of the temperature and from the blocking of a portion of the water available to the contaminants. As a general rule, these inocula remain unstable with respect to contaminants and poorly resist temperatures above about 40° C., which is a drawback in hot climates or, in general, upon preservation, due to a definite risk of contamination.

In order to control the different degradation processes (i.e., development of microorganisms, chemical reactions, enzymatic reactions, changes in texture) it is possible to act more or less selectively on each of these phenomena by controlling the customary parameters of physical chemistry, temperature, pH, redox potential, and by the use of specific inhibitors. However, these means have proven limited. This is due, in particular, to the fact that the prior art adheres to the principle that the water available must be sufficient to assure the survival of the microorganism.

It has now been discovered that, starting from the customary water activity values of 0.85 and more in inocula, if the water activity is lowered, there is an initial decrease in the development of molds and of the enzymatic reactions but that substantial plasmolysis of the cells and browning reactions occur. Similar effects are noted in going from a very low water activity to a water activity of the order of 0.85 and more. As a matter of fact, the change to intermediate water activities on the order of 0.4 to 0.8 in lethal for bacterial, whether this change is effected upon dehydration or upon rehydration. In the case of dehydration, this phenomenon has been overcome by an extremly rapid passage through this lethal region by means of freeze-drying (U.S. Pat. No. 3,168,796 to Scott) or by means of spray drying. However, this technique does not solve the problem of destruction of the microorganism under conditions of use in which rehydration is slow and progressive.

SUMMARY OF THE INVENTION

The present invention relates to a method of preparing inocula of low water activity having a long storage life and improved resistance to temperature and rehydration, according to which microorganisms of the genus Rhizobium in a culture medium containing a carbohydrate source are incorporated in a polymer gel and the water activity of the resulting inoculum is then lowered to and maintained at less than 0.1. The present invention also relates to inocula prepared according to the method of the present invention and to seeds precoated with the inocula as well as to the inoculation of soil with the inoculum.

DESCRIPTION OF THE PREFERRED EMBODIMENTS

The essence of the present invention resides in extracting the largest available fraction of water possible from the product, eliminating all the bulk water (LEUNG, H. K., 1981, Structure and Properties of Water-Cereal Food World, 26, 7-350-352) and using the characteristics of a specific mixture of gel and soluble substances in order to avoid destruction of the microorganism upon rehydration.

The process of the invention is characterized by enclosing the microorganism in its culture medium in a polymer gel and decreasing the water activity in the resulting inoculum to below 0.1 and then maintaining the water activity at this value. The different optimal values of the water activity for the protection of the microorganism upon its storage and its rehydration depend, in particular, on the temperature, the nature of the microorganism, the nature and concentration of the soluble substances present, and the type of polymer used.

The value of the water activity beyond which there is no further development of molds, enzymatic reactions, and browning reactions, depends on the conductions of the culture medium, the nature of the microorganism, and the gel. It can be assumed that, in general, a maximum number of viable cells is preserved for minimum values of $a_w$. The different values of the water activity are obtained and determined by the method of saturated aqueous solutions (Multon, 1981, Analysis and Control Techniques in the Agro-Food Industries (APRIA)).

A knowledge of the rate of destruction of the microorganisms at a particular temperature is a necessary parameter for developing a reliable method of preparing an inoculum. It has now been discovered that the resistance of the microorganisms in the inocula to elevated temperatures (60° C.) is at a maximum for the lowest water activity values and that rapid decreases in the survival rate occur at 60° C. when the water activity value is raised to 0.5.

It has also been discovered that, upon rehydration, the rate of destruction of the microorganisms at intermediate water activities on the order of 0.4 to 0.8 is a function of the carbohydrate source of the culture medium and the gel. The hypothesis can be advanced that the survival of the microorganisms is a function of the availability of water which serves the role of reagent by placing the soluble or partially soluble compounds present in the medium into solution. The mobility of these compounds, as a result of osmosis, would result in the destruction of the microorganisms.

It has further been discovered that the change in the absorption isotherms of the inocula and, therefore, the water activity, is modified by the manner of obtaining the isotherm (hysteresis phenomenon), by the temperature, by the nature of the gel, by the nature and concentration of the carbohydrate sources and the soluble substances in the culture, by the modification of the culture medium by the microorganisms, and by the crystallization of the crystallizable compounds present.

The polymer used is advantageously selected from the group of polysaccharides which have been subjected to at least a partial cross-linking treatment. By at least a partial cross-linking treatment, is meant a treatment which is capable of modifying the structure of the polysaccharide, such as heat treatment, treatment with a metal salt, preferably an iron or aluminum salt, or an alkaline earth salt, preferably a calcium salt, or treatment with another polymer, preferably another polysaccharide.

The polymer advantageously comprises a heteropolysaccharide of high molecular weight obtained by fermentation of a carbohydrate by a microorganism of the genus Xanthomonas or the genus Arthrobacter or by fungi of the genus Sclerotium. Use can also be made of polysaccharides obtained from natural or biosynthetic gums of different origins such as algae (alginates, carrageenans, agar), plant exudates (gum karaya, tragacanth, arabic) and seeds (guar, carob). The polymers may be present in various forms such as gels, balls or fibers.

The use of polymers having a polysaccharide base promotes the growth of the microorganism in the soil after inoculation in at least the following ways: the size of the polymer particles permits the best dissemination of the Rhizobium; the polysaccharide powder is rapidly rewetted; the polysaccharide binds to the particles of soil and other substrates and to the roots; and the polysaccharide is rapidly degraded in the soil, releasing the Rhizobium from their polymer matrix to infect the roots of the leguminous plant.

The culture medium of the present invention contains at least one carbohydrate source, preferably selected from the group consisting of sugars, polyols and polysaccharides. Particularly preferred as the carbohydrate source are mannitol, glucose, dextrin and starch. Also preferred as the carbohydrate source are sugars higher than $C_6$, in particular, mannitol, sorbitol or fructose. The culture medium also contains at least one inorganic salt and an organic mineral nitrogen source which does not contain high molecular weight molecules, preferably a yeast extract of the following composition:

| Component | % |
|---|---|
| Yeast Extract | |
| Amino acid | 5.5 [% Yeast Extract] |
| NaCl | 0.5 |
| Ca | 0.08 |
| Fe | 0.20 |
| K | 3.4 |
| Mg | 0.07 |
| P | 1.16 |
| Carbohydrates | 16.6 |
| Amino Acid | |
| Arginine | 3.5 [% Amino-Acid] |
| Cystine | 1.6 |
| Histidine | 1.5 |
| Isoleucine | 4.7 |
| Leucine | 6.4 |
| Lysine | 6.5 |
| Methionine | 2.0 |
| Phenylalanine | 3.5 |
| Threonine | 3.3 |
| Tryptophan | 1.0 |
| Tyrosine | 4.0 |
| Valine | 4.8 |
| Vitamins | 2.7 cg/g |

The concentration of the nitrogen source in the medium before culture is on the order of 0.1% but the extract is partially consumed during culture of the microorganism.

The total of gel, mineral salt, carbohydrate source and nitrogen source in the culture medium constitutes between 2 and 10% of the suspension to be dried, on a dry weight basis. The polymer represents between 1 and 2% of the suspension to be dried, the carbohydrate source between 0.5% and 1%, and the yeast extract between 0.05% and 1%. Before drying, additives such as those discussed above or other inert additives can be included in the suspension, provided that the total weight % of all additives is within the range of from about 2% to about 10% of the suspension to be dried, on a dry weight basis.

The microorganism used in the present invention is of the genus Rhizobium. The microorganism of the genus Rhizobium is preferably selected from the group consisting of *Rhizobium japonicum, Rhizobium meliloti, Rhizobium phaseoli, Rhizobium leguminosarum,* and *Rhizobium trifolii.*

Rhizobium are among the microorganisms most sensitive to temperature and dehydration. It is known that the gram negative bacteria are particularly sensitive to dessication (Soil Biol. Biochem., Vol. 14, pp. 13–14 (1982)) and the Rhizobium confirm this statement. Among the species of Rhizobium, *Rhizobium japonicum* USDA 138 has been described by F. Munevar (Applied and Environmental Microbiology, August 1981, pages 272–276) as having a maximum survival temperature of 39.1° C. This microorganism, contrary to many others which are heat resistant, such as, for instance, the Bacillus, cannot, according to the prior art, be dried at high temperature without endangering the survival of the microorganism. The preferred culture medium for the growth of *Rhizobium japonicum* is the YEM medium, a conventional medium containing yeast extract which is well known to those skilled in the art.

According to the method of the present invention for preparation of the inoculum, the bacteria are grown in the culture medium, the culture medium is combined with the polysaccharide gel and the gel is then dried. The inoculum is preferably prepared in powder or microgranulate form in order to facilitate its use. The bacterial concentration can be increased by centrifuging the culture medium and then placing the bacterial deposit in suspension. The culture medium can be added to the polysaccharide or the polysaccharide dissolved in the culture medium.

The inoculum can be deposited on a support such as one having a base of silica. In the event that a method involving an absorbent such as silica is used, this absorbent may, furthermore, serve the function of support and inert filler, facilitating the use and handling of the inoculum.

Drying can be effected in various ways and in one or more steps. However, simply contacting the gel with air under the customary conditions of temperature and relative humidity is not sufficient. A technique must be used which makes it possible to obtain a more exhaustive drying, such as: (1) contacting the gel with a dry, hot air stream, under conditions compatible with the survival of the microorganism; or (2) contacting the gel with a saturated solution of a compound having the required water activity, developing towards equilibrium with the inoculum.

Preferably, a spray-drying technique is employed which, unexpectedly, leads to inocula in which the survival of the microorganism is preserved even if the temperatures of the treatment gases are far greater than those which the microorganism can withstand. When spray drying is employed, the gel must be a free-flowing gel. The cross-linking of the polymer can be effected simultaneously by the heat treatment employed to effect drying. The various acceptable drying techniques can be combined.

From an economical standpoint, it is preferred to use a two-stage drying system such as that employed for the dehydration of milk. This system consists of a spraydrying stage which, when effected with an outlet temperature of about 95° C., leads to a water activity in the inoculum on the order of 0.2 to 0.4, followed by a fluidized-bed stage which dries the inoculum to a water activity of less than 0.1. The use of a two-stage system makes it possible to increase the rate of flow of the substance to be dried and therefore the difference in temperature between the outlet and the inlet. The solution which enters the sprayer may be subjected to a temperature of 250° C. and more without destroying the microorganisms. The outlet temperature which is preferably within the range of about 75° C. to about 95° C. is maintained above the dew point, which avoids rehydration of the products. The fluidized bed used to complete the drying and reach a water activity of less than 0.1 consumes two to four times less energy for the elimination of the last fraction of water than does spray drying, realizing an overall energy savings on the order of 20%.

One advantage of the present invention is that it is possible to include fungicidal products in the inoculum without any alteration of the bacterial cell. The products which can be used within the inoclum are those such as thirame and aluminum ethyl phosphite. At water activities of less than 0.1, there is no loss of the microorganism due to the presence of the fungicide.

The transfer of water to the low water activity inoculum during storage from the surrounding atmosphere should be limited by the selection of a suitable method of packaging. The principal characteristic of a suitable packaging is its impermeability to water vapor. This presupposes that the packaging has been effected such that there is no microporosity or leakage microchannels at the seals. In the packaging, water-vapor equilibrium is established between the internal atmosphere and the inoculum; once this equilibrium is reached, the water absorption capacity of the inoculum becomes negligible (very low ratio of kg of air to kg of product). Polypropylene films such as Pryphane (marketed by R. P. Films) constitute a suitable packaging material. The polypropylene films assure good thermal stability (non-conductivity, non-reflectivity), low transmission of light, and good permeability to gases. If desired, a dehydrating agent may be included in the package.

By means of the present invention it has been possible to preserve Rhizobium for a period of at least two years without any detectable loss.

EXAMPLES

The following examples present illustrative embodiments of the present invention. Comparative data is also presented.

Xanthan-carob gel inoculums (A, B, C, D, E and F), an alginate-CaCl$_2$ polymeric inoculum (G), and an alginate-CaSO$_4$ (gel) polymeric inoculum (H) were prepared as follows.

EXAMPLE 1

Xanthan-carob gel inoculum. The following ingredients were combined:

| Ingredient | Wt. % |
|---|---|
| culture medium - YEM medium carbohydrate source | 10.0 |

-continued

| Ingredient | Wt. % |
|---|---|
| DIFCO yeast extract | 1.0 |
| K$_2$HPO$_4$ | 0.5 |
| MgSO$_4$.7H$_2$O | 0.2 |
| FeCl$_3$ | 0.004 |
| NaCl | 0.2 | the pH adjusted to 6.8 with HCl, and the resultant culture medium sterilized at 120° C. The six inocula varied only in the carbohydrate source added to the culture medium.

| Inoculum | Carbohydrate Source |
|---|---|
| A | mannitol |
| B | glycerol |
| C | glucose syrup DE40 |
| D | glucose syrup DE33 |
| E | dextrin |
| F | soluble starch. |

Rhizobium japonicum was used (strain G$_3$ USDA 138 Beltsville).

The number of Rhizobium per milliliter of culture after incubation for 6 days in the culture medium was on the order of 2 to 3×10$^9$.

Two solutions were perpared (the values are given for the preparation of 300 g of inoculum).

(a) Polysaccharide solution of the anionic type resulting from the fermentation of carbohydrates by a microorganism of the genus Xanthomonas of MW 2×10$^6$, which will be referred to as Product 1. 100 ml of distilled water were brought to 70°–80° C. and 1.5 g of Product 1 were added. This temperature was maintained for 20–30 minutes with agitation and then reduced to between 40° to 50° C.

(b) Solution of carob flour=polysaccharide formed of β-D-manno pyranosyl units (bonds 1–4) one out of four or five being substituted at C$_6$ by an α-D-galactopyranosyl MW=3.1×10$^5$, which will be referred to as Product 2. 100 ml of distilled water were brought to 70°–80° C. and 1.5 g of Product 2 were added. This temperature was maintained for 20–30 minutes with agitation and then reduced to between 40° and 50° C.

When the solutions were at 40°–45° C., 50 ml of the bacterial culture were added to each of them with agitation. The mixture of culture and polysaccharide was then poured, with vigorous agitation, into the mixture of culture medium and carob flour. A consistent gel was obtained instantaneously if the two solutions were vigorously mixed.

EXAMPLE 2

Inoculum A prepared as in example 1 and two inocula which were identical except that one contained thiram and the other contained aluminum ethyl phosphite were prepared and portions of each dried to six different water activity values. The eighteen samples were stored for 30 days at 25° C. and the number of Rhizobium/g remaining determined. The results are summarized below in Table I.

TABLE I

| TREATMENT | Log of the number of Rhizobium/g after 30 days of storage (25° C.)* | | | | | |
|---|---|---|---|---|---|---|
| | Water Activity | | | | | |
| | 0.06 | 0.22** | 0.39** | 0.43** | 0.52** | 0.75** |
| Inoculum A without thiram*** | 7.82 | 7.74 | 7.43 | 7.39 | 0 | 0 |
| Inoculum A with thiram in the proportions (1:2) | 8.83 | 8.62 | 8.04 | 7.97 | 5.65 | 0 |
| Inoculum A/ aluminum ethyl phosphite (1:1) | 8.81 | 0 | 0 | 0 | 0 | 0 |

*Log of the number of Rhizobium/g of inoculum before storage: 9.04.
**Comparative.
***Thiram: bis-(dimethyl-thiocarbamyl)disulfide a.m. 90% solubility: 30 ppm.

EXAMPLE 3

Alginate-$CaCl_2$ polymeric inoculum. A culture medium was prepared as in example 1 using mannitol as the carbohydrate source. Inoculum G was prepared according to the following three essential steps:

(1) Preparation of the suspension of Rhizobium in the alginate. 2 g of sodium alginate of low viscosity (130–240 cps) were dissolved in 100 ml of bacterial culture.

(2) Gelation. The suspension of Rhizobium in the alginate was dropped into a solution of $CaCl_2.2H_2O$ (170 g/L). Gelation took place in balls if the suspension was added drop by drop to the solution of $CaCl_2.2H_2O$ with agitation. The gelation took place in fibers if 20 ml of the $CaCl_2.2H_2O$ solution were poured with agitation into the alginate solution.

(3) Washing. Immediately after gelation, the polymeric inoculum in balls (or in fibers) was washed in running water.

EXAMPLE 4

Alginate-$CaSO_4$ (gel) polymeric inoculum. A culture medium was prepared as in example 1 using mannitol as the hydrocarbon source. Inoculum H was prepared according to the following two essential steps:

(1) Preparation of the suspension of Rhizobium in an alginate of a viscosity of between 750 and 1000 cps. One gram of alignate was dissolved in 80 ml of bacterial culture. For this purpose the powder was dispersed in a fine rain onto the culture while continuously agitating it until the alginate was completely solubilized.

(2) Gelation. 20 ml of a solution of $CaSO_4.2H_2O$ at 6 g/L were added to the suspension of Rhizobium in the alginate. The gel set instantaneously.

In the following examples 5 through 12, the water activity of the inocula was adjusted by using saturated solutions. The water activities of the saturated solutions at 25° C. are set forth below in Table II.

TABLE II

| Solutes (saturated solutions) | Value of $a_w$ at 25° C. | |
|---|---|---|
| NaOH | 0.0695 | |
| Actigel | 0.11 | |
| $MgCl_2$ | 0.3273 | 0.332 |
| $CrO_3$ | 0.396 | |
| $K_2CO_3 2H_2O$ | 0.438 | 0.4276 |
| Mg $(NO_3)_2$ | 0.5288 | |
| $Na_2Cr_2O_7$ | 0.535 | |
| NaBr | 0.5770 | |
| $CuCl_2$ | 0.886 | |
| $NaNO_3$ | 0.7373 | |
| NaCl | 0.7532 | |
| KCl | 0.8432 | |
| $KNO_3$ | 0.920 | |
| $NH_4H_2PO_4$ | 0.927 | |

EXAMPLE 5

Figure 1:
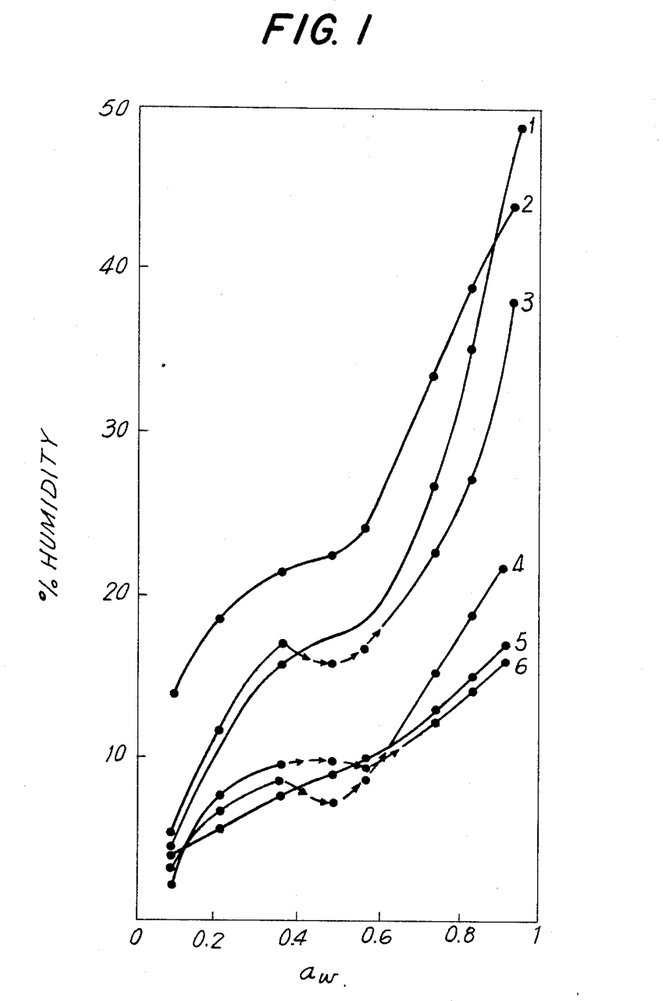
FIG. 1 shows the absorption isotherms at 25° C. of inocula B (curve 1), G (curve 2), A (curve 3), and of inocula formed of freeze-dried Rhizobium cells (curve 4), of vacuum-dehydrated Rhizobium cells (curve 5), and of an inoculum on peat (curve 6). The small arrows show the crystallization phenomenon of the mannitol.

The water activity as a function of % humidity was plotted for six different inocula and is presented in FIG. 1 wherein:

| Curve No and type of inoculum | Carbohydrate Source | Gel | Type of drying |
|---|---|---|---|
| 1 (B) | glycerol | xanthan carob gum | in air |
| 2 (G) | mannitol | alginate | in air |
| 3 (A) | mannitol | xanthan carob | in air |
| 4* | mannitol | none | freeze-drying |
| 5* | mannitol | none | dehydration under vacuum |
| 6* | mannitol | none | on peat |

*Comparative.

The small arrows indicate the phenomenon of crystallization of the mannitol.

EXAMPLE 6

Figure 2:
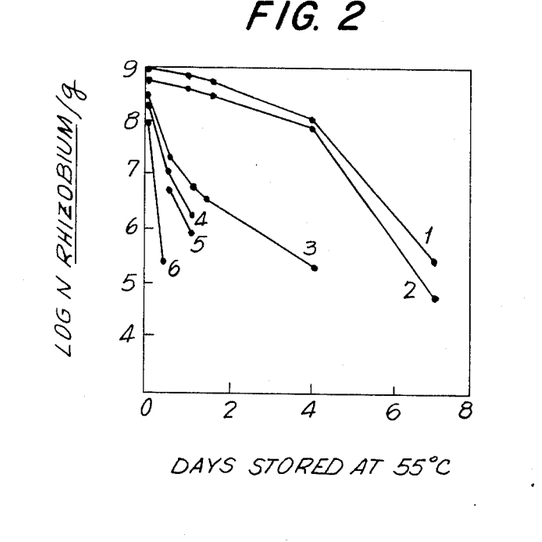
FIG. 2 shows the effect of temperature (55° C.) during storage on the survival rate of Rhizobium in inoculum A as a function of $a_w$ (curve 1, $a_w=0.09$; curve 2, $a_w=0.11$; curve 3, $a_w=0.22$; curve 4, $a_w=0.32$; curve 5, $a_w=0.43$; curve 6, $a_w=0.52$).
Figure 3:
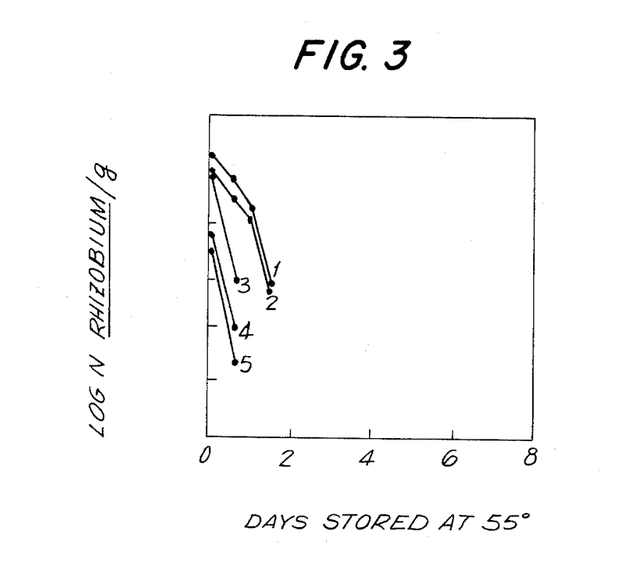
FIG. 3 shows the effect of temperature (55° C.) during storage on the survival of Rhizobium in inoculum B as a function of $a_w$ (curve 1, $a_w=0.09$; curve 2, $a_w=0.11$; curve 3, $a_w=0.22$; curve 4, $a_w=0.32$; curve 5, $a_w=0.43$; curve 6, $a_w=0.52$).

The data obtained for the survival rate of Rhizobium in inoculum A and inoculum B during storage at 55° C. over an 8 day period as a function of water activity are presented in FIG. 2 and FIG. 3, respectively. (Curve 1, $a_w$=0.09; curve 2, $a_w$=0.11; curve 3, $a_w$=0.22; curve 4, $a_w$=0.32; curve 5, $a_w$=0.43; curve 6, $a_w$=0.52). FIG. 2 and FIG. 3 show that the preservation of the microorganisms is much better with a $C_6$ sugar than with a $C_3$ sugar.

EXAMPLE 7

Figure 4:
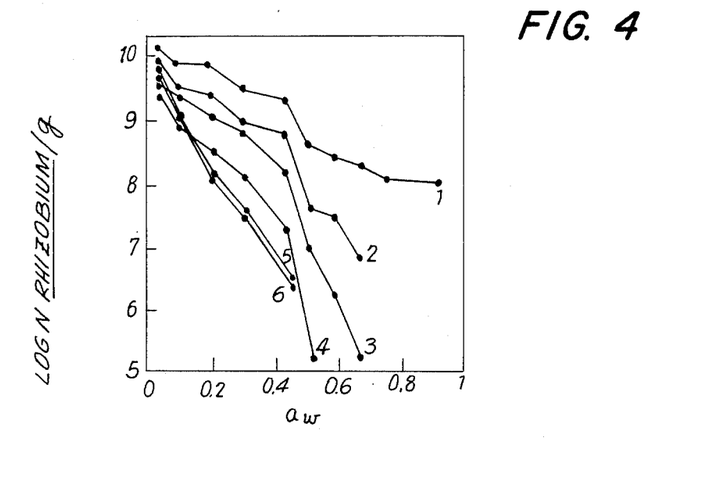
FIG. 4 shows the survival rate of Rhizobium in inoculum A as a function of $a_w$ after different storage times at 25° C. (curve 1: 10 days; curve 2: 20 days; curve 3: 30 days; curve 4: 80 days; curve 5: 110 days; curve 6: 180 days).

FIG. 4 shows the survival rate of Rhizobium in inoculum A (xanthan carob and mannitol) as a function of $a_w$ after different storage times at 25° C. (curve 1=10 days; curve 2=20 days; curve 3=30 days; curve 4=80 days; curve 5=110 days; curve 6=180 days).

EXAMPLE 8

Figure 5:
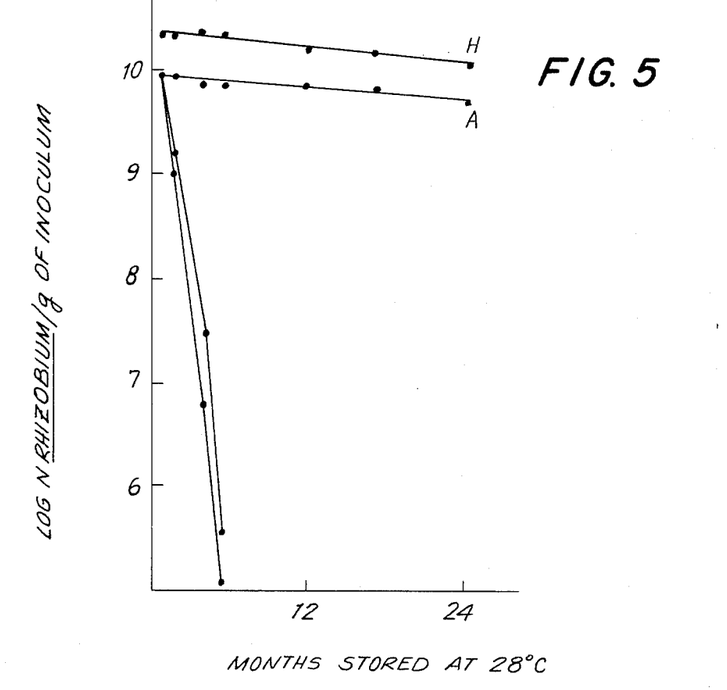
FIG. 5 shows the survival rate of Rhizobium in inoculum A and in inoculum H as a function of time and different values of $a_w$ (curve 1, $a_w=0.06$; curve 2, $a_w=0.42$).

FIG. 5 shows the survival rate of Rhizobium during storage at 28° C. in inoculum A (xanthan, carob and mannitol) and in inoculum H (alginate and mannitol) as a function of time and different values of $a_w$ (curve I: $a_w$=0.06; curve II: $a_w$=0.42). There is no significant difference in the survival rate of Rhizobium for the different polysaccharides.

EXAMPLE 9

Figure 6:
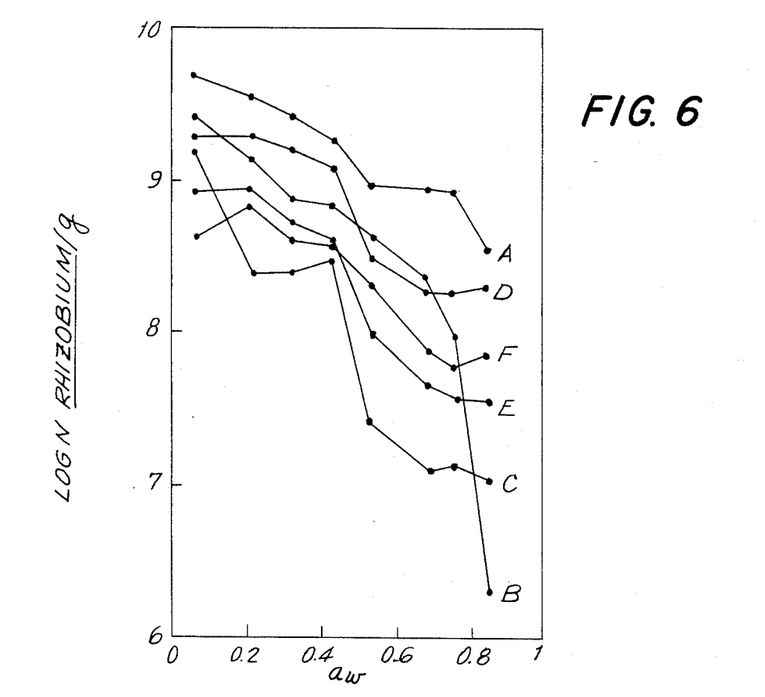
FIG. 6 shows the survival rate of Rhizobium in inocula A, B, C, D, E, and F as a function of $a_w$ after 10 days of storage at 28° C. and shows the effect of different carbon sources of different molecular weights on the survival rate of Rhizobium.

FIG. 6 illustrates the survival rate or Rhizobium as a function of the carbohydrate source in the culture medium and the $a_w$ value after storage for 10 days at 28° C. In FIG. 6:

curve A=mannitol
curve B=glycerol
curve C=glucose DE 40
curve D=glucose DE 33
curve E=dextrin
curve F=starch

EXAMPLE 10

Figure 7:
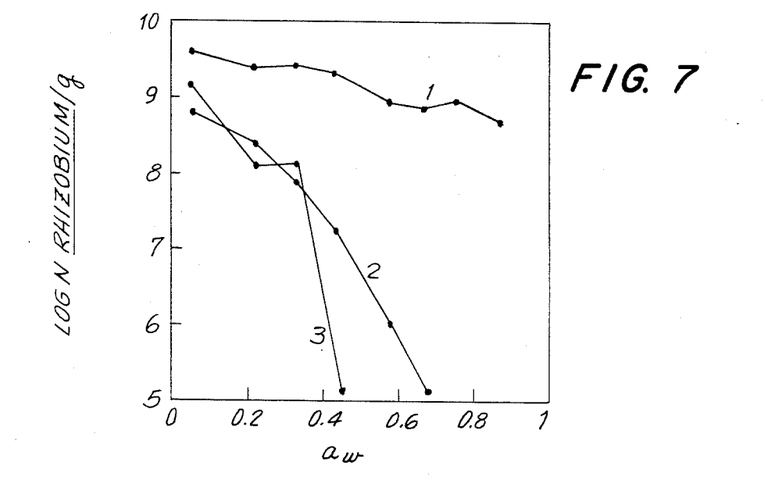
FIG. 7 shows the survival rate of three strains of Rhizobium in inoculum A after 10 days of storage at 28° C. (curve 1: *Rhizobium japonicum* USDA 138 Beltsville; curve 2: *Rhizobium meliloti* 2011, INRA DIJON; curve 3: *Rhizobium phaseoli* strain Olivia University of Minnesota, U.S.A.).

FIG. 7 shows the survival rate of three strains of Rhizobium in inoculum A after 10 days of storage at 28° C. (curve 1 *Rhizobium japonicum* USDA 138 Beltsville; curve 2 *Rhizobium meliloti* 2011, INRA DIJON; curve 3 *Rhizobium phaseoli* strain Olivia University of Minnesota, USA).

EXAMPLE 11

Figure 8:
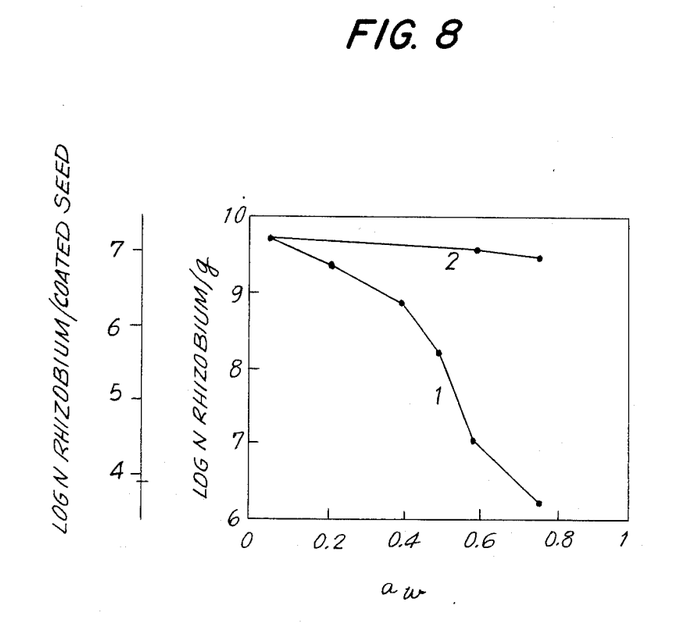
FIG. 8 shows the survival rate of *Rhizobium japonicum* in inoculum A on soybeans precoated with the inoculum (Culfivar Kingsoy), as a function of $a_w$, and at two temperatures (curve 1, 28° C.; curve 2, 4° C.) after 60 days of storage.

FIG. 8 shows the survival rate of *Rhizobium japonicum* in inoculum A on soybeans precoated with the inoculum (Culhvar Kingsoy) as a function of $a_w$ at two temperatures (curve 1, 28° C.; curve 2, 4° C) after 60 days of storage.

EXAMPLE 12

Inocula A and H were dried using a turbine sprayer (such as is described in the book by Masters, Spray Drying—Second Edition, John Wiley & Sons 1976). Employing an outlet temperature of 75° C. and varying the inlet temperature between 150° and 250° C., it was noted that the log in Rhizobium living per gram of sprayed powder remained stable and equal to the initial value, that is, $10^{10}$ Rhizobium per gram. Accordingly, there was no destruction of the Rhizobium and an inoculum in powder form was obtained.

We claim:

1. A method of preparing an inoculum having a long storage life, and improved resistance to temperature and rehydration, comprising preparing a culture medium containing microorganisms of the genus Rhizobium and at least one carbohydrate in a polymer gel and then exhaustively drying the gel by contacting the gel with a dry, hot air stream, under conditions compatible with the survival of the microorganisms to lower the water activity of the resulting inoculum to and maintaining the water activity at less than 0.1.

2. The method of claim 1 wherein the polymer is a polysaccharide.

3. The method of claim 2 wherein the polysaccharide is partially cross-linked by a method selected from the group consisting of thermal treatment, treatment with a metal salt, and treatment with another polymer.

4. The method of claim 2 wherein the polysaccharide is a heteropolysaccharide having a base of xanthan gum and carob flour.

5. The method of claim 2 wherein the polysaccharide is an alginate-base polysaccharide.

6. The method of claim 1 wherein the carbohydrate is selected from the group consisting of sugars, polyols, and polysaccharides.

7. The method of claim 6 wherein the carbohydrate is selected from the group consisting of sugars and polyols having at least six carbons.

8. The method of claim 7 wherein the carbohydrate is selected from the group consisting of mannitol, sorbitol, glucose, fructose, dextrin, and starch.

9. The method of claim 1 wherein the culture medium includes a nitrogen source.

10. The method of claim 9 wherein the nitrogen source is yeast extract.

11. The method of claim 1 wherein the culture medium includes at least one inorganic salt.

12. The method of claim 1 wherein the microorganism is *Rhizobium japonicum.*

13. The method of claim 1 wherein the drying comprises spray drying.

14. The method of claim 1 wherein the drying comprises spray drying followed by passage over a fluidized bed.

15. The method of claim 1 wherein the inoculum includes fungicide.

16. The method of claim 1 wherein the carbohydrate is from about 0.5 to 1 percent of the inoculum on a dry weight basis.

17. The method of claim 1 wherein the hot air stream has a temperature of at least 75° C.

18. An inoculum prepared according to the method of claim 1 wherein the polymer is a polysaccharide that is at least partially cross-linked and the carbohydrate is selected from the group consisting of mannitol, sorbitol, fructose, glucose, dextrin, and starch.

19. A method comprising coating seeds with the inoculum of claim 18.

20. A method comprising inoculating soil with the inoculum of claim 18.

21. A seed coated with the inoculum of claim 18.

* * * * *

UNITED STATES PATENT AND TRADEMARK OFFICE
CERTIFICATE OF CORRECTION

PATENT NO. : 4,755,468
DATED : July 5, 1988
INVENTOR(S) : Gerard Jung and Jacques Mugnier It is certified that error appears in the above-identified patent and that said Letters Patent is hereby corrected as shown below:

Col. 2, line 67, "in" should be -- is --;

Col. 4, line 25, "conductions" should be -- conditions --, and

Claim 15, line 32, insert "a" before -- fungicide --.

Signed and Sealed this

Twenty-ninth Day of January, 1991

Attest:

HARRY F. MANBECK, JR.

*Attesting Officer*  *Commissioner of Patents and Trademarks*